US011055447B2

(12) United States Patent
Jain et al.

(10) Patent No.: US 11,055,447 B2
(45) Date of Patent: Jul. 6, 2021

(54) METHODS AND SYSTEMS FOR ADAPTIVE PARAMETER SAMPLING

(71) Applicant: Tata Consultancy Services Limited, Mumbai (IN)

(72) Inventors: Prachin Lalit Jain, Thane (IN); Sanat Sarangi, Thane (IN); Prakruti Vinodchandra Bhatt, Thane (IN); Srinivasu Pappula, Hyderabad (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 349 days.

(21) Appl. No.: 16/231,203

(22) Filed: Dec. 21, 2018

(65) Prior Publication Data

US 2019/0362027 A1 Nov. 28, 2019

(30) Foreign Application Priority Data

May 28, 2018 (IN) .............................. 201821019941

(51) Int. Cl.
*G06F 13/10* (2006.01)
*G06F 30/00* (2020.01)
*H04L 29/08* (2006.01)
*G01N 33/24* (2006.01)
*G01W 1/04* (2006.01)
*G01W 1/14* (2006.01)
*G01N 33/00* (2006.01)

(52) U.S. Cl.
CPC ......... *G06F 30/00* (2020.01); *G01N 33/0098* (2013.01); *G01N 33/246* (2013.01); *G01N 2033/245* (2013.01); *G01W 1/04* (2013.01); *G01W 1/14* (2013.01); *H04L 67/12* (2013.01)

(58) Field of Classification Search
CPC .................................................. G06F 17/5018
USPC ............................................................ 703/2
See application file for complete search history.

(56) References Cited

U.S. PATENT DOCUMENTS

| 8,180,471 | B2 * | 5/2012 | Good | G05B 19/41875 |
| | | | | 700/108 |
| 9,009,001 | B2 * | 4/2015 | Vass | G05B 9/02 |
| | | | | 702/179 |

(Continued)

OTHER PUBLICATIONS

Pavón-Pulido, N. et al. (2017). "New trends in precision agriculture: a novel cloud-based system for enabling data storage and agricultural task planning and automation," *Precision Agric.*, vol. 18; pp. 1038-1068.

(Continued)

*Primary Examiner* — Andy Ho
(74) *Attorney, Agent, or Firm* — Finnegan, Henderson, Farabow, Garrett & Dunner LLP

(57) ABSTRACT

This disclosure relates to precision agriculture that relies on monitoring micro-climatic conditions of a farm to make accurate disease forecasts for better crop protection and improve yield efficiency. Conventional systems face challenge in managing energy and bandwidth of transmission considering the humongous volume of data generated in a field through IoT based sensors. The present disclosure provides energy-efficient adaptive parameter sampling from the field by optimally configuring the parameter sampling rate thereby maximizing energy-efficiency. This helps reduce unnecessary traffic to a cloud while extending network lifetime.

14 Claims, 5 Drawing Sheets

(56) References Cited

U.S. PATENT DOCUMENTS 9,792,557 B2 10/2017 Mathur et al.
2017/0127622 A1 5/2017 Hong

OTHER PUBLICATIONS

Khattab, A. "Design and Implementation of a Cloud-based IoT Scheme for Precision Agriculture," *2016 28th International Conference on Microelectronics (ICM)*, Dec. 17-20, 2016, Giza, Egypt; 5 pages.

* cited by examiner

METHODS AND SYSTEMS FOR ADAPTIVE PARAMETER SAMPLING

PRIORITY CLAIM

This U.S. patent application claims priority under 35 U.S.C. § 119 to: Indian Patent Application No. 201821019941, filed on 28 May 2018. The entire contents of the aforementioned application are incorporated herein by reference.

TECHNICAL FIELD

The disclosure herein generally relates to precision farming and, more particularly, to methods and systems for adaptive sampling of parameters resulting in energy efficient Internet of Things (IoT) deployments.

BACKGROUND

It is seen that every year farmers lose a large volume of their crops due to various diseases caused by unfavorable environmental circumstances. Accurate forecasting of diseases requires continuous monitoring of these conditions especially for micro-climatic environment of the crop. Sensors play a critical role in forecasting. With sensors becoming pervasive, there are now bigger Wireless Sensor Network (WSN) deployments in agricultural fields. This increases the volume of data from sensor nodes to a gateway. As data keeps flowing in at regular intervals of time, a huge chunk of data gets offloaded to a cloud system for further analyses which increases traffic and load on the server. Power for outdoor IoT deployments for agriculture has constraints. To obtain a scalable solution, this may include reliance on solar power as a source of power for the sensor nodes. Also, collecting and transmitting data at a higher-than-required frequency drains precious power while increasing resource consumption for storage and network.

SUMMARY

Embodiments of the present disclosure present technological improvements as solutions to one or more of the above-mentioned technical problems recognized by the inventors in conventional systems.

In an aspect, there is provided a processor implemented method comprising: sampling via a plurality of sensor nodes, a pre-defined set of agronomic and agromet parameters that govern onset of one or more diseases in one or more crops under consideration in at least one agricultural area, at a current sampling rate, the sampled parameters being associated with a crop identifier corresponding to the one or more crops under consideration; labelling, by a pre-trained disease prediction model, the sampled parameters as one of favorable or unfavorable for the one or more diseases based on heuristic thresholds associated thereof, the pre-trained disease prediction model being a linear classifier or a non-linear classifier depending on number of feature vectors comprising the sampled parameters and data points thereof; analyzing change in label of the sampled parameters over a first time period, by an analyzer, to identify a valid change in label, the first time period being dependent on at least one of the sampled parameters, an associated crop or an associated disease under consideration. The step of analyzing comprises: computing weighted moving average (WMA) of the data points sampled for the first time period, wherein a new data point is given a higher weight compared to an earlier data point; computing a standard deviation (std) of the data points used for computing the WMA; if a data point lies beyond the WMA±k*std, the data point is an outlier and does not contribute to the valid change in label, where k is a pre-defined multiplier to configure the range WMA±std depending on the sampled parameter; and if a data point lies within the WMA±k*std, the data point contributes to the valid change in label. This is followed by adapting the current sampling rate based on the identified valid change in label by a sampling rate controller wherein the step of adapting the current sampling rate comprises: maintaining the current sampling rate if there is no valid change in label of the sampled parameters; checking a confidence level of the label for each of the data points contributing to the valid change in label, for a second time period, wherein the second time period is based on minimum time taken to revert a trend of change in the data points associated with a sampled parameter; and reducing the current sampling rate if the valid change in label results in the unfavorable label; or increasing the current sampling rate if the valid change in label results in the favorable label. In an embodiment, the method above further comprises obtaining feedback from the at least one agricultural area by a re-training module, the feedback comprising the crop identifier and confirmation or correction of the predicted severity level of the one or more diseases; and updating the pre-trained disease prediction model based on the obtained feedback.

In another aspect, there is provided a system comprising: one or more data storage devices operatively coupled to the one or more processors and configured to store instructions configured for execution by the one or more processors to: sample via a plurality of sensor nodes, a pre-defined set of agronomic and agromet parameters that govern onset of one or more diseases in one or more crops under consideration in at least one agricultural area, at a current sampling rate, the sampled parameters being associated with a crop identifier corresponding to the one or more crops under consideration; label, by executing a pre-trained disease prediction model comprised therein, the sampled parameters as one of favorable or unfavorable for the one or more diseases based on heuristic thresholds associated thereof, the pre-trained disease prediction model being a linear classifier or a non-linear classifier depending on number of feature vectors comprising the sampled parameters and data points thereof; analyze change in label of the sampled parameters over a first time period, by executing an analyzer comprised therein, to identify a valid change in label, the first time period being dependent on at least one of the sampled parameters, an associated crop or an associated disease under consideration, wherein, the change in label of the sampled parameters is analyzed by: computing weighted moving average (WMA) of the data points sampled for the first time period, wherein a new data point is given a higher weight compared to an earlier data point; computing a standard deviation (std) of the data points used for computing the WMA; if a data point lies beyond the WMA±k*std, the data point is an outlier and does not contribute to the valid change in label, where k is a pre-defined multiplier to configure the range WMA±std depending on the sampled parameter; and if a data point lies within the WMA±k*std, for a second time period, the data point contributes to the valid change in label, wherein the second time period is based on minimum time taken to revert a trend of change in the data points associated with a sampled parameter; adapt the current sampling rate based on the identified valid change in label of the sampled parameters over the first time period by executing a sampling rate controller comprised therein, wherein the current sampling rate is adapted by: maintaining the current sampling rate if there is no valid change in label of the sampled parameters; checking a confidence level of the label for each of the data points contributing to the valid change in label, for the second time period; and reducing the current sampling rate if the valid change in label results in the unfavorable label; or increasing the current sampling rate if the valid change in label results in the favorable label; obtain feedback from the at least one agricultural area by executing a re-training module comprised therein, the feedback comprising the crop identifier and confirmation or correction of the predicted severity level of the one or more diseases; and update the pre-trained disease prediction model based on the obtained feedback.

In yet another aspect, there is provided a computer program product comprising a non-transitory computer readable medium having a computer readable program embodied therein, wherein the computer readable program, when executed on a computing device, causes the computing device to: sample via a plurality of sensor nodes, a pre-defined set of agronomic and agromet parameters that govern onset of one or more diseases in one or more crops under consideration in at least one agricultural area, at a current sampling rate, the sampled parameters being associated with a crop identifier corresponding to the one or more crops under consideration; label, by executing a pre-trained disease prediction model comprised therein, the sampled parameters as one of favorable or unfavorable for the one or more diseases based on heuristic thresholds associated thereof, the pre-trained disease prediction model being a linear classifier or a non-linear classifier depending on number of feature vectors comprising the sampled parameters and data points thereof; analyze change in label of the sampled parameters over a first time period, by executing an analyzer comprised therein, to identify a valid change in label, the first time period being dependent on at least one of the sampled parameters, an associated crop or an associated disease under consideration, wherein, the change in label of the sampled parameters is analyzed by: computing weighted moving average (WMA) of the data points sampled for the first time period, wherein a new data point is given a higher weight compared to an earlier data point; computing a standard deviation (std) of the data points used for computing the WMA; if a data point lies beyond the WMA±k*std, the data point is an outlier and does not contribute to the valid change in label, where k is a pre-defined multiplier to configure the range WMA±std depending on the sampled parameter; and if a data point lies within the WMA±k*std, for a second time period, the data point contributes to the valid change in label, wherein the second time period is based on minimum time taken to revert a trend of change in the data points associated with a sampled parameter; adapt the current sampling rate based on the identified valid change in label of the sampled parameters over the first time period by executing a sampling rate controller comprised therein, wherein the current sampling rate is adapted by: maintaining the current sampling rate if there is no valid change in label of the sampled parameters; checking a confidence level of the label for each of the data points contributing to the valid change in label, for the second time period; and reducing the current sampling rate if the valid change in label results in the unfavorable label; or increasing the current sampling rate if the valid change in label results in the favorable label; obtain feedback from the at least one agricultural area by executing a re-training module comprised therein, the feedback comprising the crop identifier and confirmation or correction of the predicted severity level of the one or more diseases; and update the pre-trained disease prediction model based on the obtained feedback.

In an embodiment of the present disclosure, the pre-defined set of agronomic parameters include crop specific information, terrain and vegetation information; and the pre-defined set of agromet parameters include temperature, humidity, pressure, wind speed, rainfall and solar radiation.

In an embodiment of the present disclosure, the pre-trained disease prediction model is an ensemble of decision trees.

In an embodiment of the present disclosure, the one or more hardware processors are further configured to execute the pre-trained prediction model to predict severity level of the one or more diseases based on the sampled parameters over time, the severity level being normal if the sampled parameters are labelled as unfavorable, the severity level being exceptional or extreme if the sampled parameters are labelled as favorable depending on the time for which the favorable label persists.

In an embodiment of the present disclosure, the one or more hardware processors are further configured to execute the sampling rate controller to increase the current sampling rate more when the predicted severity level is extreme as compared to the predicted severity level being exceptional when the sampled parameters are labelled as favorable.

In an embodiment of the present disclosure, the pre-trained disease prediction model is pre-trained with noise in the form of incorrect labels due to at least one of disease reporting error and incorrect sensor values.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
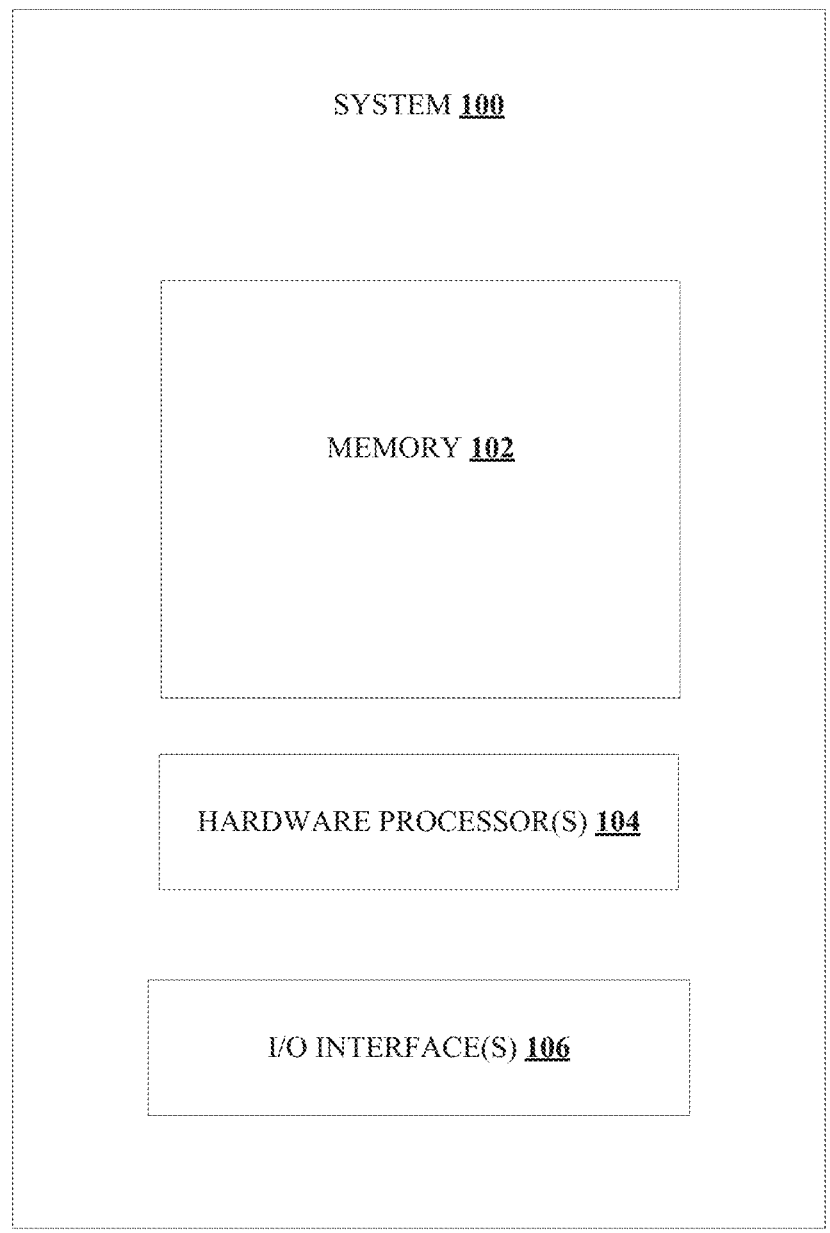
FIG. 1 illustrates an exemplary block diagram of a system for adaptive parameter sampling, in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Agriculture is one of the key growth-pillars of a country. Every year farmers lose a large volume of their crops to pests and diseases. Diseases caused by unfavorable environment circumstances can be detected and avoided by closely examining parameters such as soil moisture, temperature, relative humidity, rainfall, and leaf-wetness. For example, worldwide production loss of potato due to Late Blight disease is estimated to be worth €12 billion. To address this situation, significant work has been done worldwide in developing models that predict such diseases which then helps in their prevention or timely remedial action. Internet of Things (IoT) in agriculture uses Wireless Sensor Networks (WSN) as key building blocks for precision farming. With sensors becoming pervasive, there are big deployments connected over the web which increases the amount of data being transmitted.

In a method proposed by Jain A and Chang E. Y., in a paper titled "Adaptive sampling for sensor networks," Kalman-Filter (KF) is employed to estimate sensor values wherein sensors can use KF estimation error to adaptively adjust its sampling rate within a given range autonomously such that the rate of sampling increases if the error is higher than a pre-defined error margin. In another energy-aware flood warning system, the sampling rate is adapted based on the predicted flood situation using a hydraulic model coupled to a KF. In this system, when the probability of water exceeding a threshold (flood situation) is less than 5%, the requirement of transmitting data from sensor nodes is lowered thus reducing activity of individual nodes and minimizing data volume to help prolong the network lifetime. In case of farming, lower rate of sampling at onset of events like disease or pest infestation can delay actions necessary for reducing yield loss. Some intervention at the gateway is therefore required which can monitor crops as per requirements and take necessary actions to mitigate risk at critical cultivation stages.

The present disclosure provides methods and systems for adaptive parameter sampling at edge devices such as gateways, routers or any other network hardware that regulates traffic by intelligently sampling parameters based on specific disease conditions in order to improve energy efficiency of a field-deployed network. The overall effect is enhanced lifetime of the network and reduced burden on power sources and computing resources at the farm under consideration and a cloud system by logging only absolutely essential information.

In the context of the present disclosure, the expressions 'farm' and 'agricultural area' may be used interchangeably. The expression 'gateway' used hereinafter in the description refers generally to any network hardware serving as an edge device and that regulates traffic between sensor nodes and a cloud system in a WSN. Besides regulating traffic, the system of the present disclosure deployed on the gateway provides intelligence that leads to adaptive sampling or parameters resulting in an energy efficient, resource efficient, just-in-time responses for precision agriculture.

Referring now to the drawings, and more particularly to FIGS. 1 through 4, where similar reference characters denote corresponding features consistently throughout the figures, there are shown preferred embodiments and these embodiments are described in the context of the following exemplary system and method.

FIG. 1 illustrates an exemplary block diagram of a system 100 for adaptive parameter sampling in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

The I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or nonvolatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2:
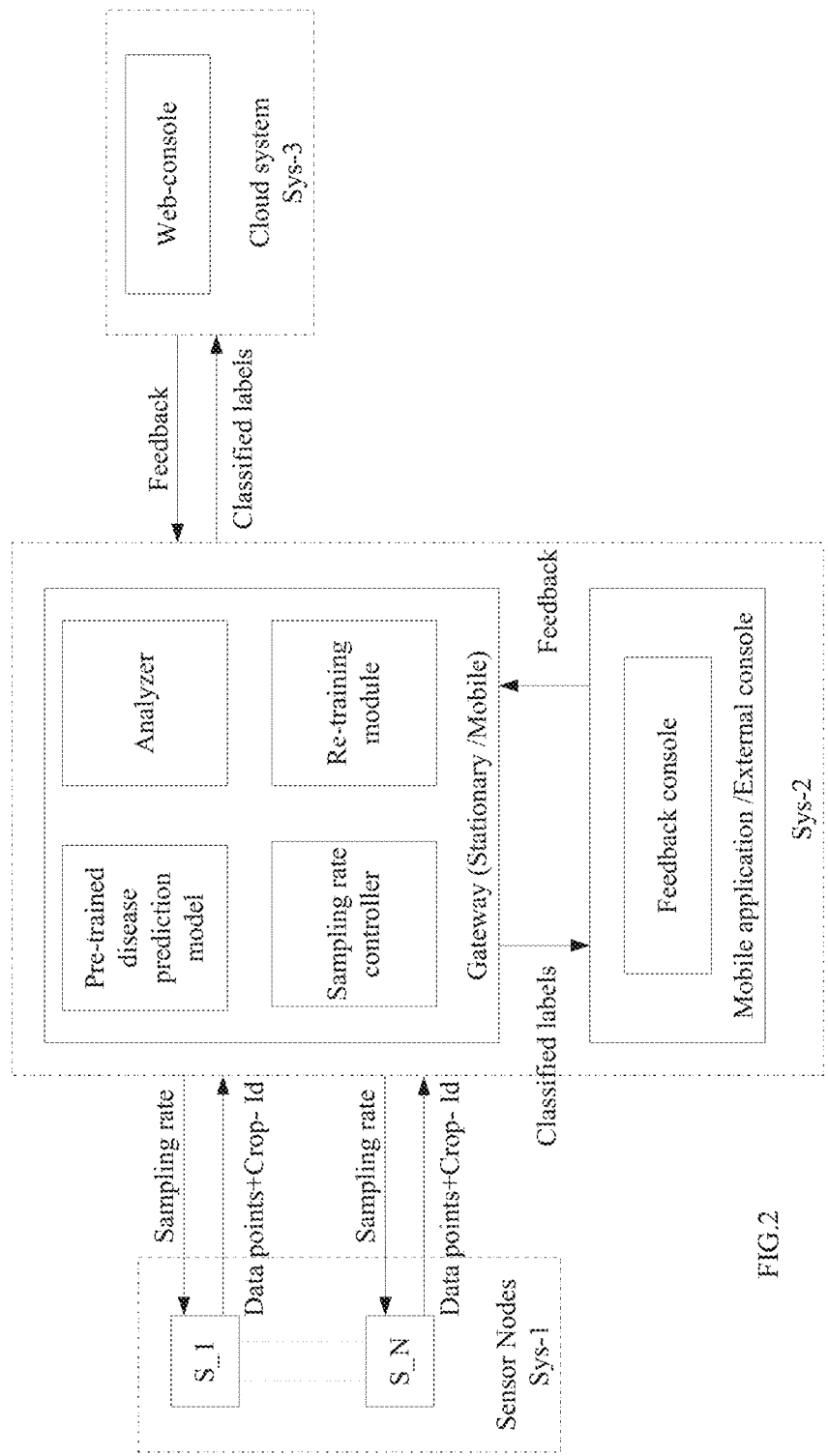
FIG. 2 illustrates architecture of an exemplary implementation of the system for adaptive parameter sampling, in accordance with an embodiment of the present disclosure.

FIG. 2 illustrates architecture of an exemplary implementation of the system 100 for adaptive parameter sampling, in accordance with an embodiment of the present disclosure. An exemplary WSN is illustrated with exemplary flow of information that may be deployed in at least one agricultural area having one or more crops under consideration. The exemplary implementation may have three sub-systems viz., Sys-1 wherein sensor nodes are deployed, Sys-2 comprising a stationary or mobile gateway and Sys-3 comprising a cloud system. In an embodiment, the Sys-1 is set-up in one or more agricultural areas at different locations for sensing ambient and crop parameters like temperature, relative humidity, leaf wetness and the like. The sensor values are communicated to the Sys-2 over wired or wireless communication. A current sampling rate is varied based on input received from the Sys-2. In an embodiment, the Sys-2 may be connected to an external feedback console if stationary or the feedback console may already be available as part of a mobile application for receiving feedback from the farm. The Sys-2, if stationary, may also independently communicate with the mobile application and use the mobile as a console for feedback. In an embodiment, the Sys-3 may also be provided with a web console for feedback.

In an embodiment, the gateway of Sys-2 is located between the sensor nodes and the cloud system and is configured to have communication, processing and storage facility. It manages both downstream communication with the sensor nodes and upstream communication with a mobile application/console and the cloud system.

Figure 3A:
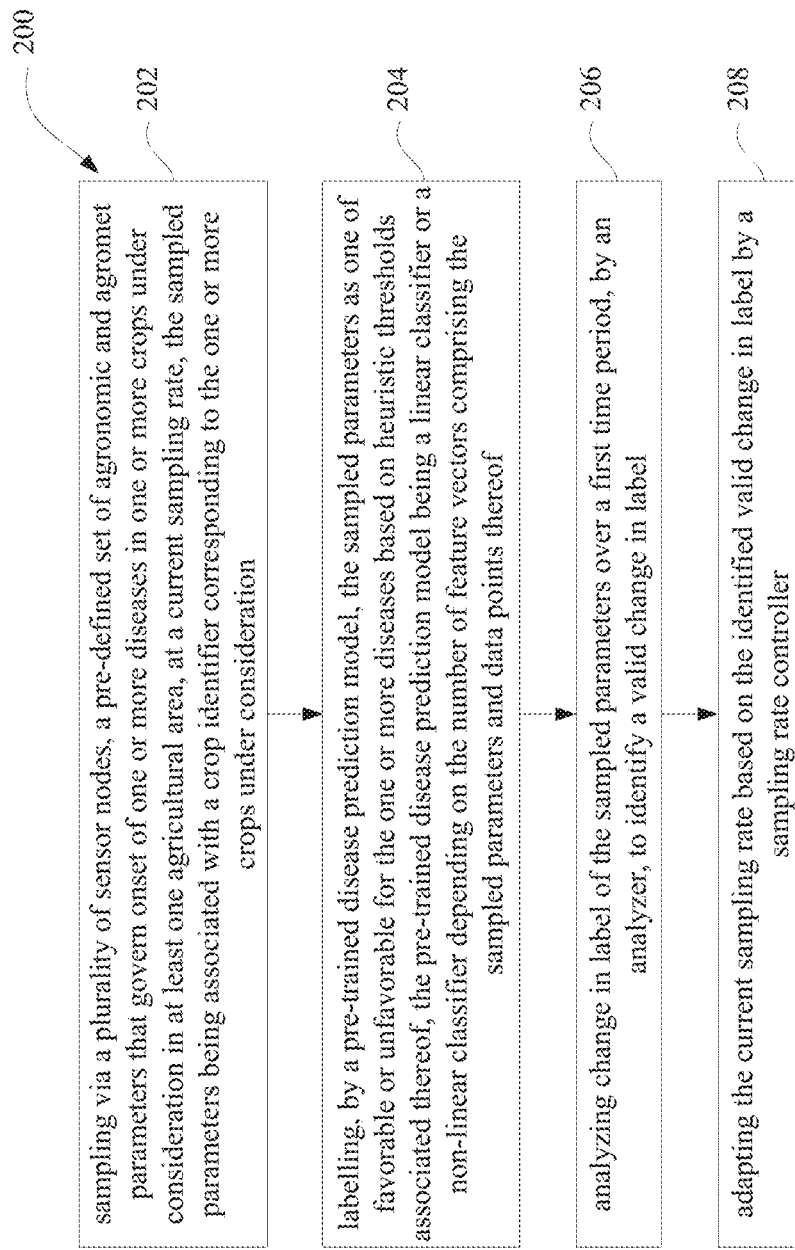
FIG. 3A through FIG. 3B illustrate exemplary flow charts for a computer implemented method for adaptive parameter sampling, in accordance with an embodiment of the present disclosure.
Figure 3B:
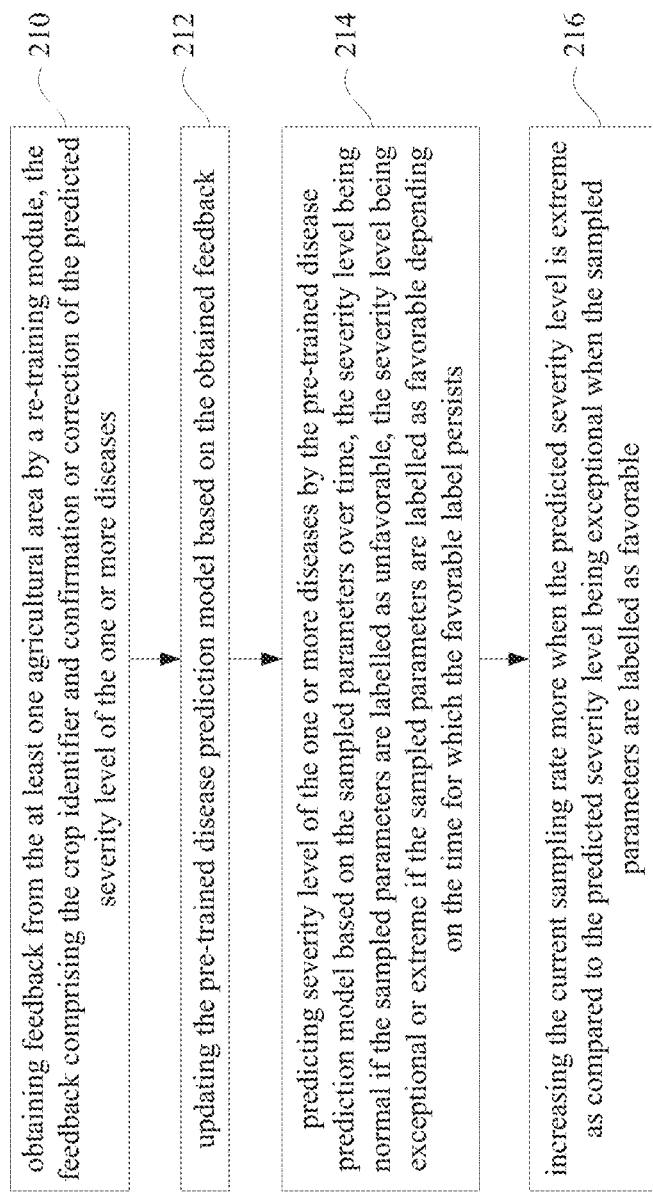

FIG. 3A through FIG. 3B illustrate exemplary flow charts for a computer implemented method for adaptive parameter sampling, in accordance with an embodiment of the present disclosure. In an embodiment, the system 100 includes one or more data storage devices or memory 102 operatively coupled to the one or more processors 104 and is configured to store instructions configured for execution of steps of the method 200 by the one or more processors 104. The steps of the method 200 will now be explained in detail with reference to the components of the system 100 of FIG. 1 and the exemplary architecture of FIG. 2. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

Accordingly, in an embodiment of the present disclosure, the one or more processors 104 are configured to sample via a plurality of sensor nodes, at step 202, a pre-defined set of agronomic and agromet parameters that govern onset of one or more diseases in one or more crops under consideration in at least one agricultural area, at a current sampling rate. The sensor nodes (S_1 through S_N) may be deployed as part of Sys-1 of FIG. 2. In accordance with the present disclosure, the pre-defined set of agronomic parameters may include crop specific information, terrain and vegetation information. Also, the pre-defined set of agromet parameters may include temperature, humidity, pressure, wind speed, rainfall and solar radiation. In an embodiment, the sampled parameters may be associated with a crop identifier (Crop-Id) corresponding to the one or more crops under consideration.

In accordance with an embodiment of the present disclosure, the one or more processors 104 are configured to label, at step 204, the sampled parameters as one of favorable or unfavorable for the one or more diseases. In an embodiment, the one or more processors 104 performing step 204 may be implemented in the form of a pre-trained disease prediction model in Sys-2 of FIG. 2. In accordance with an embodiment of the present disclosure, the pre-trained disease prediction model has a two-class classification output {favorable, unfavorable} based on heuristic thresholds associated with the sampled parameters. Conventional systems have relied on the heuristic thresholds alone. It may be understood by those skilled in the art that the thresholds for parameters conducive to pest or disease conditions may not be static and have undergone changes due to various resistant varieties of pests and diseases that have developed over time, global warming induced changes and agroclimatic zones being differ from place to place. These dynamics are addressed by the pre-trained disease prediction model of the present disclosure that baselines on the heuristic thresholds and then makes the classification relevant and accurate via continuous learning and updation by a feedback mechanism. Learnings over seasons, across crop varieties and varying agroclimatic zones are updated in the pre-trained disease prediction model making it adaptive for implementation across multiple crops and multiple farms simultaneously. Furthermore, dependency on domain experts for labelling the parameters is also reduced.

In accordance with the present disclosure, the pre-trained disease prediction model is crop and farm adaptive thereby maximizing the network lifetime while maintaining a given service level agreement from the farmers perspective. Table 1 shows an exemplary list of crops and heuristic thresholds associated with some of their diseases based on studies that are primarily dependent on two parameters—temperature and humidity.

TABLE 1

Heuristic thresholds for crop disease

| Crop | Temp (P1) | Relative Humidity (P2) | Disease |
| --- | --- | --- | --- |
| Potato | 10° C.-30° C. | >80% | Late Blight |
| Tomato | 10° C.-35° C. | >90% | Powdery Mildew |
| Banana | 27° C.-30° C. | >70% | Black Sigota |
| Onion | 6° C.-32° C. | 93-100% | Downy Mildew (P. Destructor) |
| Rice | 28° C.-32° C. | 96-100% | Sheath Blight |
| Wheat | 20° C.-30° C. | 85% | Fusarium Head Blight |

With a *Phytophthora infestans* model for Potato Late Blight, a relative humidity above 80% is conducive for sporulation. If that happens, calculation for infection severity levels starts if air temperature is between 10° C. and 30° C., and it is raining Accordingly, when temperature is sampled and has a value between 10° C. and 30° C., it may contribute towards classifying the sampled parameter temperature as favourable for the disease Potato Late Blight. Powdery Mildew of Tomato is caused by relative humidity levels exceeding 90% and for temperature range between 10° C. and 35° C. Similarly every disease or pest related to a crop has a certain temperature and relative humidity range associated with it where it starts proliferating and may contribute to the sampled parameter being classified as favorable. Table 1 merely depicts 2 parameters. In real world scenario, there may be several parameters conducive to diseases or pests that need to be monitored closely. Such monitoring of multiple crop varieties in different agricultural areas keeping in mind the varying heuristic thresholds over time is a technical challenge that is addressed in the present disclosure.

In accordance with an embodiment of the present disclosure, the pre-trained disease prediction model may be firstly trained with prior assumptions about conditions conducive for pest and disease growth. The pre-trained disease prediction model may be a linear classifier or a non-linear classifier depending on number of feature vectors comprising the sampled parameters (for instance, temperature, relative humidity, etc.) and associated data points (number of sampled parameters). For a training dataset with few number of features as well as limited data points, a linear classifier like support vector machines (SVM) may be chosen. Similarly an ensemble of decision trees may be chosen when the number of features and number of data points are high. Artificial neural network (ANN) based classifier may be chosen when the number of features are less and number of data points are high. As may be understood by persons skilled in the art, these are general guidelines with non-specific limitation to number (high, few, limited, less) and users may employ any classifier depending on the desired accuracy of classification. In the event that the pre-trained disease prediction model is an ensemble of decision trees, the data points may be passed through each decision tree which is trained to classify the data points as belong to a favorable or unfavorable class for disease escalation. Class wise votes are aggregated and the class receiving maximum votes is chosen as a final class. If a linear classifier like SVM is employed, then distance from a separating plane may be considered. Likewise if ANN is employed, a probability value may be considered for deciding the final class.

Since critical periods associated with diseases require measurements to be taken on the ground at relatively frequent intervals to enable near real-time or just-in-time action by farmers, in accordance with the present disclosure, the gateway is provided with intelligence to react to the thresholds associated with such parameters either for individual crops or for a group of crops serviced by it. A resultant effect is an increase the sampling frequency where it is required and cut down on redundant sampling for non-essential parameters. This type of variable sampling rate helps not only in reduction of energy consumption but also reduces data traffic to the cloud system (Sys-3 of FIG. 2) when compared to a uniform sampling strategy. It may be noted that there is a two-fold reduction in traffic—from the sensor nodes (Sys-1) to the gateway (Sys-2) and from the gateway (Sys-2) to the cloud system (Sys-3).

In accordance with an embodiment of the present disclosure, the one or more processors 104 are configured to analyze, at step 206, change in label of the sampled parameters over a first time period to identify a valid change in label. In an embodiment, the one or more processors 104 performing step 206 may be implemented in the form of an analyzer in Sys-2 of FIG. 2. Identifying valid change in label comprises tracking abrupt changes between favorable and unfavorable conditions thereby ensuring reduced false alarms that may trigger a need for change in the current sampling rate in accordance with the present disclosure. Genuine changes in the sampled parameters need to be tracked for the first time period. The sampled parameters relating to environmental conditions may fluctuate near to associated thresholds and need consideration to identify whether it is a valid change. In an embodiment, the first time period is dependent on at least one of the sampled parameters, an associated crop or an associated disease under consideration.

In accordance with an embodiment of the present disclosure, the step of analyzing comprises firstly computing weighted moving average (WMA) of the data points sampled for the first time period, wherein a new data point is given a higher weight compared to an earlier data point. The WMA may be represented as given below.
$WMA = p_0 * d_n + p_1 * d_{n-1} + \ldots p_n * d_0$ where $p_0 + p_1 + \ldots p_n = 1$ and where p is weight and d is the data point, n is the number of data points considered in the first time period.

Once the WMA is computed, a standard deviation (std) of the data points used for computing the WMA is also computed. If a data point lies beyond the WMA±the k*std, the data point is an outlier and does not contribute to the valid change in label, where k is a pre-defined multiplier to configure the range WMA±std depending on the sampled parameter. If a data point lies within the WMA±k*std, the data point contributes to the valid change in label.

In accordance with the present disclosure, the one or more processors 104 are configured to adapt, at step 208, the current sampling rate based on the identified valid change in label. In an embodiment, the one or more processors 104 performing step 208 may be implemented in the form of a sampling rate controller. In an embodiment, the sampling rate controller is configured to maintain the current sampling rate if there is no valid change in label of the sampled parameters. If there is a change in label of the sampled parameters, then the confidence level of the label for each of the data points contributing to the valid change in label for a second time period is checked, wherein the second time period is based on minimum time taken to revert a trend of change in the data points associated with a sampled parameter. The current sampling rate is reduced if the valid change in label results in the unfavorable label and increased if the valid change in label results in the favorable label.

Some parameters may be periodic or seasonal in nature. But some parameters like leaf wetness are not periodic. It just reduces fast enough so that the time period for changing from wet to dry condition may be considered as the second time period since this parameter may take the minimum time to revert the trend of change among all other parameters. Many agromet parameters are co-related with temperature. So in an embodiment, the parameter temperature may be considered as a reference for deciding the second time period. Deciding on number of data points based on the second time period results in more number of samples when there is a disease condition, thus imposing a stricter condition of sampling rate reversal to non-disease condition; stricter because more number of samples contribute in the WMA and frequent check in decision making.

In accordance with an embodiment of the present disclosure, the one or more processors 104 are further configured to predict severity level of the one or more diseases, at step 214. In an embodiment, the pre-trained disease prediction model may be configured to perform step 214 based on the sampled parameters over time. In an embodiment, the severity level may be 'normal' if the sampled parameters are labelled as unfavorable; the severity level may be 'exceptional' or 'extreme' if the sampled parameters are labelled as favorable depending on the time for which the favorable label persists. Accordingly, if the favorable condition persists for a very long time, the severity level is 'extreme' and in an embodiment, the one or more processors 104 may be configured to increase the sampling rate, at step 216, such that the increase is more when the predicted severity level is extreme as compared to the predicted severity level being exceptional. Again, it may be understood by persons skilled in the domain that the expression 'long time' may be quantified based on the sampled parameter, the crop and disease being monitored.

In an exemplary embodiment, if the label is unfavorable and there is no valid change in the label, the severity level is 'normal' and the sampling period is set to say 15 min. If the label changes to favorable and the change is identified as a valid change, then severity level is 'exceptional' and the sampling period may be reduced to say 5 min. Again if the label favorable remains constant for half a day, then the severity level is 'extreme' and the sampling period may be reduced further to say 3 min. The adapted sampling rate is transmitted from Sys-2 to Sys-1 wherein the sensor nodes are implemented.

In accordance with an embodiment of the present disclosure, the one or more processors 104 may be configured to obtain feedback, at step 210, from the at least one agricultural area, wherein the feedback includes the crop identifier and confirmation or correction of the predicted severity level of the one or more diseases. In an embodiment, the one or more processors 104 performing step 210 may be implemented in the form of a re-training module. The feedback is merged with a training dataset and used as a whole to update the pre-trained disease prediction model at step 212. Step 210 increases the accuracy of prediction which helps farmers take just-in-time action and avoid proliferation of crop viruses. Along with this, the overall energy efficiency of Sys-2 is also enhanced.

In accordance with an embodiment of the present disclosure, data used to pre-train the pre-trained disease prediction model may cover a wide range of all possible combinations of environmental conditions. The data may be created using sum of Gaussian distribution covering average values and variations in environmental conditions of various parts of the world. The data is labeled for disease and non-disease causing condition for different crops. In general, the data may have noise in form of incorrect labels, due to at least one of disease reporting error incorrect sensor values. This noise characteristic may also be introduced in the training data so as to make the classification model more robust to noisy input data. The assumption while adding the noise in the form of incorrect sensor values is that some but not all feature values (environmental parameters) can be wrong due to sensor malfunction. Also, the noise of type disease reporting error may be added in the form of a certain percentage of incorrect labels in the data. In accordance with an embodiment, the pre-trained disease prediction model may be trained with the data modeled with noise as well as tested with varying percentage of error to make the system 100 tolerant to outliers and capable of reacting to noise in a predictable manner.

Figure 4:
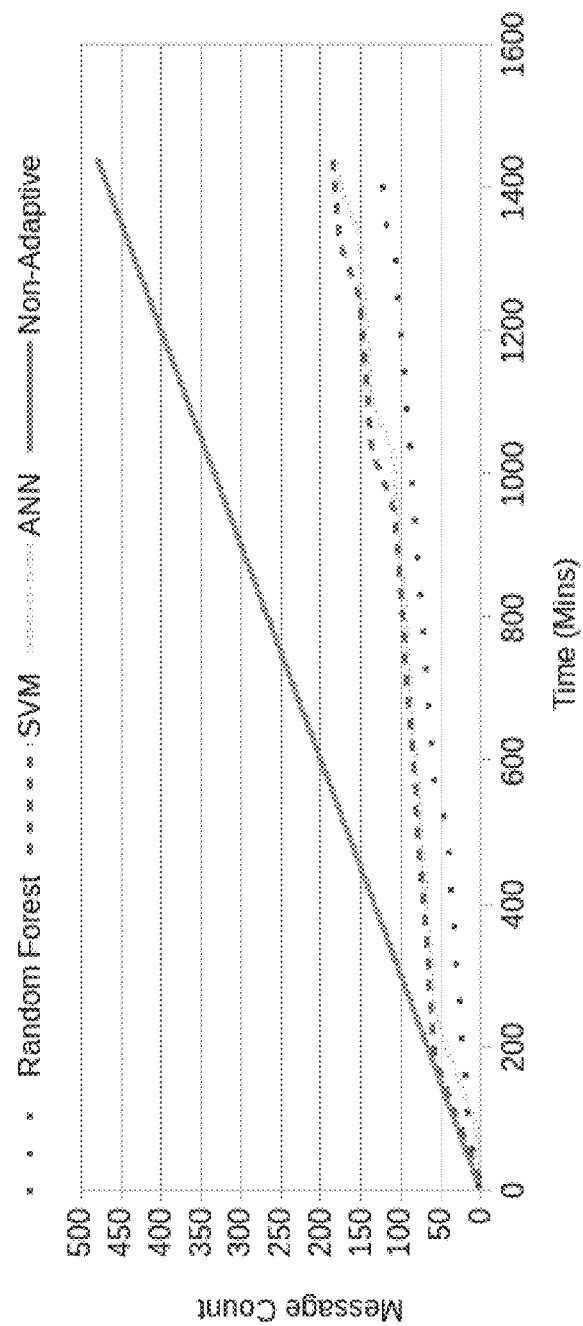
FIG. 4 illustrates energy comparison, in terms of transmitted messages, between the system performing adaptive parameter sampling in accordance with an embodiment of the present disclosure and a conventional non-adaptive system.

FIG. 4 illustrates energy comparison, in terms of transmitted messages, between the system 100 performing adaptive parameter sampling in accordance with an embodiment of the present disclosure and a conventional non-adaptive system, wherein the non-adaptive system transmits messages every 3 minutes while sampling period set for the adaptive is 3 minutes and 15 minutes for exceptional and normal condition respectively. It may be noted that for the adaptive system that was implemented using Random Forest, SVM and ANN, the energy consumption associated with the number of transmitted messages is very less compared to the energy consumption associated with the number of transmitted messages in the non-adaptive system that is seen to increase steadily.

With the proliferation of IoT and other devices that need to broadcast and connect with each other, data filtering and handling has increased exponentially. In accordance with the present disclosure, systems and methods are provided to make edge devices such as the gateways effective and intelligent by analyzing data at the edge and shrinking the amount of data being pushed to cloud systems. Also, due to limited availability of power in developing regions, a gateway equipped with such intelligence makes itself and the field-network energy efficient and enhances their lifetime. Systems and methods of the present disclosure adjust and adapt agricultural sensing requirements to optimize the utilization of resources at the farm under consideration. Again, as compared to the prior art wherein the feedback mechanism is used to decide on the sampling rate based on error between the predicted sensor data value and actual value which can be resource intensive (battery, processing power and memory), in accordance with the present disclosure, the sampling rate is based on contextual significance of the data points as explained in the method 200 herein above.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method comprising:

sampling via a plurality of sensor nodes, a pre-defined set of agronomic and agromet parameters that govern onset of one or more diseases in one or more crops under consideration in at least one agricultural area, at a current sampling rate, the sampled parameters being associated with a crop identifier corresponding to the one or more crops under consideration;

labelling, by a pre-trained disease prediction model, the sampled parameters as one of favorable or unfavorable for the one or more diseases based on heuristic thresholds associated thereof, the pre-trained disease prediction model being a linear classifier or a non-linear classifier depending on number of feature vectors comprising the sampled parameters and data points thereof;

analyzing change in label of the sampled parameters over a first time period, by an analyzer, to identify a valid change in label, the first time period being dependent on at least one of the sampled parameters, an associated crop or an associated disease under consideration, the step of analyzing comprising:

computing weighted moving average (WMA) of the data points sampled for the first time period, wherein a new data point is given a higher weight compared to an earlier data point;

computing a standard deviation (std) of the data points used for computing the WMA;

if a data point lies beyond the WMA±k*std, the data point is an outlier and does not contribute to the valid change in label, where k is a pre-defined multiplier to configure the range WMA±std depending on the sampled parameter; and if a data point lies within the WMA±k*std, the data point contributes to the valid change in label;

adapting the current sampling rate based on the identified valid change in label by a sampling rate controller wherein the step of adapting the current sampling rate comprises:

maintaining the current sampling rate if there is no valid change in label of the sampled parameters;

checking a confidence level of the label for each of the data points contributing to the valid change in label for a second time period, wherein the second time period is based on minimum time taken to revert a trend of change in the data points associated with a sampled parameter; and reducing the current sampling rate if the valid change in label results in the unfavorable label; or increasing the current sampling rate if the valid change in label results in the favorable label;

obtaining feedback from the at least one agricultural area by a re-training module, the feedback comprising the crop identifier and confirmation or correction of a predicted severity level of the one or more diseases and updating the pre-trained disease prediction model based on the obtained feedback.

2. The processor implemented method of claim 1, wherein the pre-defined set of agronomic parameters include crop specific information, terrain and vegetation information;

and the pre-defined set of agromet parameters include temperature, humidity, pressure, wind speed, rainfall and solar radiation.

3. The processor implemented method of claim 1, wherein the pre-trained disease prediction model is an ensemble of decision trees.

4. The processor implemented method of claim 1 further comprising predicting severity level of the one or more diseases by the pre-trained disease prediction model based on the sampled parameters over time, the severity level being normal if the sampled parameters are labelled as unfavorable, the severity level being exceptional or extreme if the sampled parameters are labelled as favorable depending on the time for which the favorable label persists.

5. The processor implemented method of claim 1 further comprising increasing the current sampling rate more when the predicted severity level is extreme as compared to the predicted severity level being exceptional when the sampled parameters are labelled as favorable.

6. The processor implemented method of claim 1, wherein the pre-trained disease prediction model is pre-trained with noise in the form of incorrect labels due to at least one of disease reporting error and incorrect sensor values.

7. A system comprising:

one or more data storage devices operatively coupled to one or more hardware processors and configured to store instructions for execution by the one or more hardware processors to:

sample via a plurality of sensor nodes, a pre-defined set of agronomic and agromet parameters that govern onset of one or more diseases in one or more crops under consideration in at least one agricultural area, at a current sampling rate, the sampled parameters being associated with a crop identifier corresponding to the one or more crops under consideration;

label, by executing a pre-trained disease prediction model comprised therein, the sampled parameters as one of favorable or unfavorable for the one or more diseases based on heuristic thresholds associated thereof, the pre-trained disease prediction model being a linear classifier or a non-linear classifier depending on number of feature vectors comprising the sampled parameters and data points thereof;

analyze change in label of the sampled parameters over a first time period, by executing an analyzer comprised therein, to identify a valid change in label, the first time period being dependent on at least one of the sampled parameters, an associated crop or an associated disease under consideration, wherein, the change in label of the sampled parameters is analyzed by:

computing weighted moving average (WMA) of the data points sampled for the first time period, wherein a new data point is given a higher weight compared to an earlier data point;

computing a standard deviation (std) of the data points used for computing the WMA;

if a data point lies beyond the WMA±k*std, the data point is an outlier and does not contribute to the valid change in label, where k is a pre-defined multiplier to configure the range WMA±std depending on the sampled parameter; and if a data point lies within the WMA±k*std, the data point contributes to the valid change in label;

adapt the current sampling rate based on the identified valid change in label by executing a sampling rate controller comprised therein, wherein the current sampling rate is adapted by:
  maintaining the current sampling rate if there is no valid change in label of the sampled parameters;
  checking a confidence level of the label for each of the data points contributing to the valid change in label, for a second time period, wherein the second time period is based on minimum time taken to revert a trend of change in the data points associated with a sampled parameter; and
  reducing the current sampling rate if the valid change in label results in the unfavorable label; or
  increasing the current sampling rate if the valid change in label results in the favorable label;

obtain feedback from the at least one agricultural area by executing a re-training module comprised therein, the feedback comprising the crop identifier and confirmation or correction of a predicted severity level of the one or more diseases; and update the pre-trained disease prediction model based on the obtained feedback.

8. The system of claim 7, wherein the pre-defined set of agronomic parameters include crop specific information, terrain and vegetation information; and the pre-defined set of agromet parameters include temperature, humidity, pressure, wind speed, rainfall and solar radiation.

9. The system of claim 7, wherein the pre-trained disease prediction model is an ensemble of decision trees.

10. The system of claim 7, wherein the one or more hardware processors are further configured to execute the pre-trained prediction model to predict severity level of the one or more diseases based on the sampled parameters over time, the severity level being normal if the sampled parameters are labelled as unfavorable, the severity level being exceptional or extreme if the sampled parameters are labelled as favorable depending on the time for which the favorable label persists.

11. The system of claim 10, wherein the one or more hardware processors are further configured to execute the sampling rate controller to increase the current sampling rate more when the predicted severity level is extreme as compared to the predicted severity level being exceptional when the sampled parameters are labelled as favorable.

12. The system of claim 7, wherein the pre-trained disease prediction model is pre-trained with noise in the form of incorrect labels due to at least one of disease reporting error and incorrect sensor values.

13. A computer program product comprising a non-transitory computer readable medium having a computer readable program embodied therein, wherein the computer readable program, when executed on a computing device, causes the computing device to:
  sample via a plurality of sensor nodes, a pre-defined set of agronomic and agromet parameters that govern onset of one or more diseases in one or more crops under consideration in at least one agricultural area, at a current sampling rate, the sampled parameters being associated with a crop identifier corresponding to the one or more crops under consideration;
  label, by executing a pre-trained disease prediction model comprised therein, the sampled parameters as one of favorable or unfavorable for the one or more diseases based on heuristic thresholds associated thereof, the pre-trained disease prediction model being a linear classifier or a non-linear classifier depending on number of feature vectors comprising the sampled parameters and data points thereof;
  analyze change in label of the sampled parameters over a first time period, by executing an analyzer comprised therein, to identify a valid change in label, the first time period being dependent on at least one of the sampled parameters, an associated crop or an associated disease under consideration, wherein, the change in label of the sampled parameters is analyzed by:
    computing weighted moving average (WMA) of the data points sampled for the first time period, wherein a new data point is given a higher weight compared to an earlier data point;
    computing a standard deviation (std) of the data points used for computing the WMA;
    if a data point lies beyond the WMA±k*std, the data point is an outlier and does not contribute to the valid change in label, where k is a pre-defined multiplier to configure the range WMA±std depending on the sampled parameter; and
    if a data point lies within the WMA±k*std, the data point contributes to the valid change in label;
  adapt the current sampling rate based on the identified valid change in label by executing a sampling rate controller comprised therein, wherein the current sampling rate is adapted by:
    maintaining the current sampling rate if there is no valid change in label of the sampled parameters;
    checking a confidence level of the label for each of the data points contributing to the valid change in label, for a second time period, wherein the second time period is based on minimum time taken to revert a trend of change in the data points associated with a sampled parameter; and
    reducing the current sampling rate if the valid change in label results in the unfavorable label; or
    increasing the current sampling rate if the valid change in label results in the favorable label;
  obtain feedback from the at least one agricultural area by executing a re-training module comprised therein, the feedback comprising the crop identifier and confirmation or correction of a predicted severity level of the one or more diseases; and
  update the pre-trained disease prediction model based on the obtained feedback.

14. The computer program product of claim 13, wherein the computer readable program further causes the computing device to perform one or more of:
  predict severity level of the one or more diseases by the pre-trained disease prediction model based on the sampled parameters over time, the severity level being normal if the sampled parameters are labelled as unfavorable, the severity level being exceptional or extreme if the sampled parameters are labelled as favorable depending on the time for which the favorable label persists; and
  increase the current sampling rate more when the predicted severity level is extreme as compared to the predicted severity level being exceptional when the sampled parameters are labelled as favorable.

* * * * *